United States Patent [19]

Okahara et al.

[11] Patent Number: 5,160,450
[45] Date of Patent: Nov. 3, 1992

[54] SURFACE-ACTIVE AGENTS HAVING TWO HYDROPHOBIC CHAINS AND TWO HYDROPHILIC GROUPS

[75] Inventors: Mitsuo Okahara, Kawanishi; Araki Masuyama, Suita, both of Japan

[73] Assignee: Lion Corporation, Tokyo, Japan

[21] Appl. No.: 622,473

[22] Filed: Dec. 5, 1990

[51] Int. Cl.$^5$ .................. C11D 17/00; C11D 1/12; C11D 1/755; C07C 305/00

[52] U.S. Cl. ............ 252/174.21; 252/174.22; 252/550; 252/DIG. 17; 558/26; 558/156; 568/616; 568/623; 568/624; 568/679

[58] Field of Search ........... 252/550, 174.21, 174.22, 252/DIG. 17; 558/26, 156; 568/616, 623, 624, 679

[56] References Cited

U.S. PATENT DOCUMENTS 4,917,993  4/1990  Mukunoki et al. .................. 430/523

FOREIGN PATENT DOCUMENTS

| | | |
|---|---|---|
| 2038061 | 11/1982 | Fed. Rep. of Germany . |
| 54-12310 | 1/1979 | Japan . |
| 64-00147 | 1/1989 | Japan . |
| 64-14263 | 1/1989 | Japan . |
| 1-304033 | 12/1989 | Japan . |
| 647929 | 2/1985 | Switzerland . |
| 1374419 | 11/1974 | United Kingdom . |

Primary Examiner—A. Lionel Clingman
Assistant Examiner—William S. Parks
Attorney, Agent, or Firm—Birch, Stewart, Kolasch & Birch

[57] ABSTRACT

Novel surface active agents in the form of compounds of formulas (I) and (II) show higher surface activity.

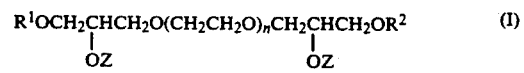

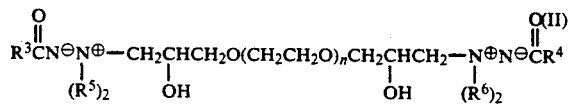

$R^1$ and $R^2$ are alkyl or alkenyl groups having 6 to 20 carbon atoms, Z is H, $SO_3H$, $PO(OH)_2$, $CH_2COOH$, $(CH_2)_2SO_3H$ or a salt thereof, $R^3$ and $R^4$ are alkyl or alkenyl groups having 5 to 19 carbon atoms, $R^5$ and $R^6$ are alkyl groups having 1 to 4 carbon atoms, and n is a number of from 1 to 20.

18 Claims, No Drawings

SURFACE-ACTIVE AGENTS HAVING TWO HYDROPHOBIC CHAINS AND TWO HYDROPHILIC GROUPS

This invention relates to surface-active agents, and more particularly, to surface-active agents having two hydrophobic chains and two hydrophilic groups exhibiting properties suitable as emulsifiers, detergents, dispersants and solubilizing agents for use in the fields of industrial, cosmetic, domestic and medical goods.

BACKGROUND OF THE INVENTION

In the prior art, a wide variety of surface-active agents including anionic, cationic, nonionic and ampholytic types are known. Most of the known surface-active agents have a basic structure bearing a hydrophilic group and a hydrophobic moiety of a single or multi-chain structure and do not necessarily exert their full function. There exists a need for the development of a surface-active agent having a higher degree of function.

SUMMARY OF THE INVENTION

An object of the present invention is to provide a novel and improved surface-active agent having two hydrophobic chains and two hydrophilic groups in the molecules exhibiting high surface activity.

According to the present invention, there is provided a surface-active agent comprising at least one compound selected from the group consisting of compounds of the following general formulae (I) and (II).

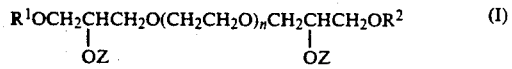

In formula (I), $R^1$ and $R^2$ are independently selected from alkyl and alkenyl groups having 6 to 20 carbon atoms, Z is selected from the group consisting of H, $SO_3H$, $PO(OH)_2$, $CH_2COOH$, $(CH_2)_2SO_3H$ and salts thereof, and n is a number of from 1 to 20.

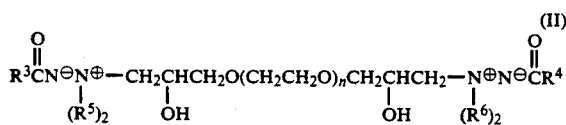

In formula (II), $R^3$ and $R^4$ are independently selected from alkyl and alkenyl groups having 5 to 19 carbon atoms, $R^5$ and $R^6$ are independently selected from alkyl groups having 1 to 4 carbon atoms, and n is a number of from 1 to 20.

DETAILED DESCRIPTION OF THE INVENTION

The surface-active agent which achieves the above and other objects of the present invention is comprised of at least one compound selected from the class consisting of compounds of general formulae (I) and (II). As compounds of the general formulae (I) and (II) can be employed either alone or in combination with one another, the relative proportion of compound (I) to compound (II) in the surface-active agent of the present invention is in the range from 100:0 to 0:100, w/w.

Compounds of formula (I)

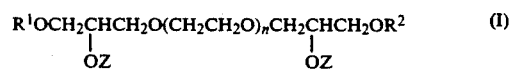

In formula (I), $R^1$ and $R^2$, which may be the same or different, are alkyl or alkenyl groups having 6 to 20 carbon atoms, preferably 6 to 12 carbon atoms. Letter n is a number of from 1 to 20, preferably 1 to 5. Z is H, $SO_3H$, $PO(OH)_2$, $CH_2COOH$, $(CH_2)_2SO_3H$ or a salt thereof, more particularly an alkali metal salt, an alkaline earth metal salt, an ammonium salt and an organic alkali salt, for example, monoethanolamine, diethanolamine, triethanolamine, trimethylamine, etc., with the alkali metal salt being preferred.

The compounds of formula (I) may be prepared by any desired methods, for example, by adding aliphatic alcohols $R^1OH + R^2OH$ to a polyalkylene glycol glycidyl ether of the following formula:

$$CH_2\underset{\diagdown O \diagup}{-}CHCH_2O(CH_2CH_2O)_nCH_2CH\underset{\diagdown O \diagup}{-}CH_2 \quad (III)$$

to form a compound of the following formula:

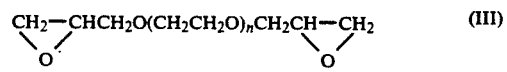

and then subjecting the compound of formula (IV) to sulfate esterification, phosphate esterification, carboxymethylation or sulfoethylation, and optionally converting into a salt. In these formulae, $R^1$, $R^2$ and n are as defined above. The sulfate esterification, phosphate esterification, carboxymethylation and sulfoethylation may be carried out by any well-known methods. The sulfate esterification may use chlorosulfonic acid, anhydrous sulfuric acid or the like; the phosphate esterification may use phosphorus pentoxide, phosphorus oxychloride, polyphosphoric acid or the like; the carboxymethylation may use α-halogenated acetate salts, α-halogenated acetate esters or the like; and the sulfoethylation may use β-halogenated ethane sulfonate salts, hydroxyethane sulfonate salts or the like.

Compounds of formula (II)

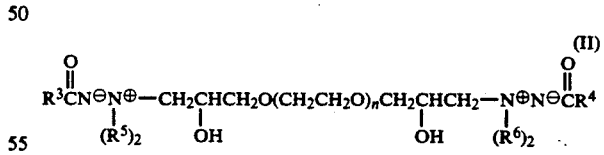

In formula (II), $R^3$ and $R^4$, which may be the same or different, are alkyl or alkenyl groups having 5 to 19 carbon atoms, preferably 5 to 11 carbon atoms, n is a number of from 1 to 20, preferably 1 to 5, and $R^5$ and $R^6$, which may be the same or different, are independently selected from alkyl groups having 1 to 4 carbon atoms, preferably 1 to 3 carbon atoms.

The compounds of formula (II) may be prepared by any desired methods, for example, by sequentially reacting a polyalkylene glycol glycidyl ether of formula (III) as defined above with dialkylhydrazines $(R^5)_2N\cdot NH_2 + (R^6)_2N\cdot NH_2$ and then with aliphatic carboxylate esters $R^3COOCH_3 + R^4COOCH_3$. In these formulae, $R^3$ to $R^6$ and n are as defined above.

The surface-active agents of the invention exhibit an extremely low critical micelle concentration (cmc) as compared with conventional surface-active agents because of the presence of two hydrophobic chains and two hydrophilic groups in their molecule. In addition, they are able to fully reduce surface tension and are highly soluble in water. By virtue of these characteristics, they will find a wide variety of applications as emulsifiers, detergents, dispersants, and solubilizing agents for use in the fields of industrial, domestic, cosmetic, and medical goods.

The surface-active agent of the invention contains at least one member of the compounds of formulae (I) and (II) as an essential component, but may be used by combining with any of conventional well-known anionic, nonionic, cationic, and ampholytic surface-active agents. Examples of the nonionic surface-active agent used herein include fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, alkanol amides, and alkylamine oxides. Examples of the anionic surface-active agent used herein include fatty acid soaps, ether carboxylic acids and salts thereof, alkane sulfonate salts, α-olefin sulfonate salts, sulfonate salts of higher fatty acid esters, higher alcohol sulfate ester salts, phosphate ester salts, condensates of higher fatty acids and amic acids, and collagen hydrolysate derivatives. Examples of the cationic surface-active agent used herein include alkyltrimethylammonium salts, dialkyldimethylammonium salts, alkyldimethylbenzylammonium salts, alkylpyridinium salts, alkylisoquinolinium salts, benzethonium chloride, and acylamino acid type cationic surface-active agents. Examples of the ampholytic surface active agent used herein include amino acid, betaine, sulfate ester, sulfonic acid, phosphate ester, an imidazoline type ampholytic surface-active agents, soybean phospholipid, and yolk lecithin.

In addition to the foregoing surface active agents, any of commonly used auxiliary additives may be added to the surface-active agents of the invention on use. Such auxiliary additives may be suitably chosen for a desired composition and generally include inorganic salts such as Glauber salt and common salt, builders, humectants, solubilizing agents, UV absorbers, softeners, chelating agents, and viscosity modifiers.

EXAMPLE

Examples of the present invention are given below by way of illustration and not by way of limitation. All parts and percents are by weight.

EXAMPLE 1

One part of ethylene glycol diglycidyl ether and 15 parts of octyl alcohol were reacted at 60° C. for 20 hours in the presence of 0.05 parts of potassium. Purification by distillation provided 1,8-bis(octyloxymethyl)-3,6-dioxaoctane-1,8-diol (boiling point 150° C./0.03 Torr) of the following formula:

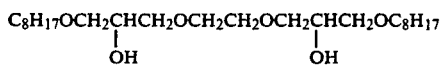

in a yield of 49%. This compound was then added to a greatly excess amount of a mixture of chlorosulfonic acid and acetic acid and reacted at room temperature for 3 hours. The resulting product was neutralized with sodium carbonate and extracted with n-butyl alcohol, obtaining a compound of the following formula:

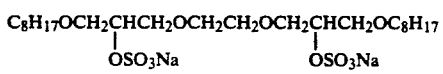

in a yield of 90%. This was a viscous liquid having a purity of 80% as measured by the modified Epton method which is a method for the quantitative measurement of anionic active agents.

EXAMPLE 2

The procedure of Example 1 was repeated except that the octyl alcohol was replaced by decyl alcohol, obtaining a compound of the following formula:

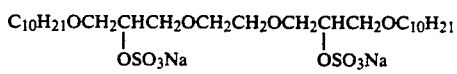

in a yield of 85%.

EXAMPLE 3

The 1,8-bis(octyloxymethyl)-3,6-dioxaoctane-1,8-diol used in Example 1 was dissolved in n-hexane. A greatly excess amount of polyphosphoric acid was added thereto dropwise, and reaction was carried out at 60° C. for 10 hours. The reaction mixture was cooled to 50° C., combined with n-hexane, water and isopropyl alcohol, and further stirred, obtaining a phosphate ester from the n-hexane phase. The reaction product was neutralized with sodium hydroxide and then extracted with water/n-butyl alcohol, obtaining a compound of the formula:

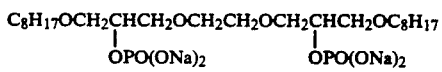

in a yield of 30%.

EXAMPLE 4

The procedure of Example 3 was repeated except that the 1,8-bis(octyloxymethyl)-3,6-dioxaoctane-1,8-diol was replaced by a compound of the following formula.

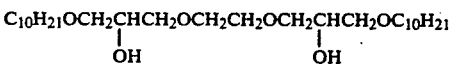

There was obtained a compound of the following formula:

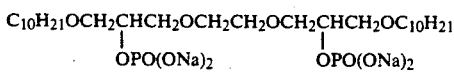

in a yield of 35%.

EXAMPLE 5

One part of the 1,8-bis(octyloxymethyl)-3,6-dioxaoctane-1,8-diol used in Example 1 was dissolved in n-butyl alcohol, 0.02 parts of metallic sodium and a greatly excess amount of bromoacetic acid were added thereto dropwise, and reaction was carried out at 75° C. for 20 hours. After purification by fractional extraction, there was obtained a compound of the formula:

$$C_8H_{17}OCH_2\underset{\underset{OCH_2COONa}{|}}{C}HCH_2OCH_2CH_2OCH_2\underset{\underset{OCH_2COONa}{|}}{C}HCH_2OC_8H_{17}$$

in a yield of 90%.

EXAMPLE 6

The procedure of Example 5 was repeated except that the 1,8-bis(octyloxymethyl)-3,6-dioxaoctane-1,8-diol was replaced by a compound of the formula:

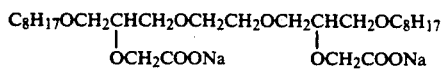

There was obtained a compound of the following formula:

$$C_{10}H_{21}OCH_2\underset{\underset{OCH_2COONa}{|}}{C}HCH_2OCH_2CH_2OCH_2\underset{\underset{OCH_2COONa}{|}}{C}HCH_2OC_{10}H_{21}$$

in a yield of 90%.

EXAMPLE 7

One part of the 1,8-bis(octyloxymethyl)-3,6-dioxaoctane-1,8-diol used in Example 1 was reacted with 1.1 parts of sodium isethionate HOCH$_2$CH$_2$SO$_3$Na at 200° C. for 2 hours in the presence of 0.03 parts of sodium hydroxide catalyst. After extraction with water/n-butyl alcohol, there was obtained a compound of the formula:

$$C_8H_{17}OCH_2\underset{\underset{OCH_2CH_2SO_3Na}{|}}{C}HCH_2OCH_2CH_2OCH_2\underset{\underset{OCH_2CH_2SO_3Na}{|}}{C}HCH_2OC_8H_{17}$$

as a white waxy solid in a yield of 50%. This product had a purity of 90% as measured by the modified Epton method.

EXAMPLE 8

The procedure of Example 7 was repeated except that the 1,8-bis(octyloxymethyl)-3,6-dioxaoctane-1,8-diol was replaced by a compound of the following formula.

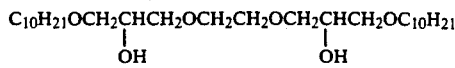

There was obtained a compound of the following formula:

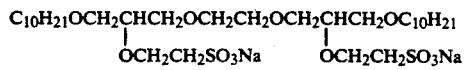

in a yield of 52%. This product had a purity of 92% as measured by the modified Epton method.

EXAMPLE 9

To a solution of 1 part of ethylene glycol diglycidyl ether in isopropyl alcohol were added 0.7 parts of dimethylhydrazine and thereafter, 2.2 parts of methyl decanoate. After reaction at room temperature for 72 hours, the reaction product was purified by column chromatography, obtaining a compound of the formula:

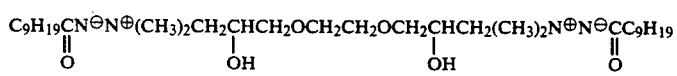

in a yield of 50%.

EXAMPLE 10

The procedure of Example 9 was repeated except that the methyl decanoate was replaced by methyl octanoate. There was obtained a compound of the formula:

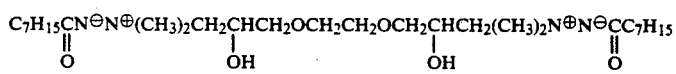

in a yield of 50%.

Aqueous solutions were prepared from the surface-active agents of Examples 1 through 10 and measured for Krafft point, critical micelle concentration, and surface tension reducing ability. The results are shown in Table 1. The surface-active agents of Examples 9 and 10 were further measured for cloud point and foam volume, which are also reported in Table 1.

The test methods are shown below.

Krafft Point

A 1% aqueous solution of a surface-active agent was prepared and visually observed for a variation in dissolved state with temperature.

Critical Micelle Concentration (cmc)

Aqueous solutions of a surface-active agent were prepared at varying concentrations. Surface tension at 20° C. was calculated by the Wilhelmy plate method to plot a surface tension vs. concentration diagram where the critical micelle concentration was determined from the bending point.

Surface Tension Reducing Ability (γcmc)

The surface tension reducing ability was determined from the surface tension at the critical micelle concentration.

Cloud Point

A 1% aqueous solution of a surface-active agent was prepared and visually observed for a variation in appearance with temperature.

Foam Volume

A 1% aqueous solution of a surface-active agent was prepared and measured by the submicron TK method.

TABLE 1

| | Krafft point (°C.) | cmc (M) | γcmc (mN·m$^{-1}$) | Remarks |
|---|---|---|---|---|
| Example 1 | <0 | 6.0 × 10$^{-4}$ | 29.2 | |
| Example 2 | <0 | 1.3 × 10$^{-5}$ | 27.0 | |
| Example 3 | <0 | 7.0 × 10$^{-4}$ | 29.2 | |
| Example 4 | <0 | 4.7 × 10$^{-5}$ | 29.0 | |
| Example 5 | <0 | 7 × 10$^{-4}$ | 29.5 | |
| Example 6 | <0 | 5 × 10$^{-5}$ | 29.0 | |
| Example 7 | <0 | 8.3 × 10$^{-4}$ | 29.5 | |
| Example 8 | <0 | 5.5 × 10$^{-5}$ | 29.0 | |
| Example 9 | — | 3.0 × 10$^{-4}$ | 30.0 | Cloud point 18.8° C., Foam volume 60 ml |
| Example 10 | — | 6.0 × 10$^{-3}$ | 32.5 | Cloud point 65.5° C., Foam volume 10 ml |
| Comparison A* | 16 | 6.8 × 10$^{-3}$ | 49.0 | cmc and γcmc measured at 50° C. |
| Comparison B* | 32 | 7.0 × 10$^{-5}$ | 41.1 | cmc and γcmc measured at 50° C. |

*A = $C_{12}H_{25}OSO_3Na$,
B = $C_{18}H_{37}O(CH_2CH_2O)_3SO_3Na$

Although some preferred embodiments have been described, many modifications and variations may be made thereto in the light of the above teachings. It is therefore to be understood that within the scope of the appended claims, the invention may be practiced otherwise than as specifically described.

We claim:

1. A surface-active agent, comprising at least one compound selected from the group consisting of a compound of the following general formula (I):

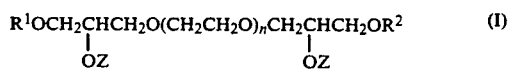

wherein $R^1$ and $R^2$ are independently selected from alkyl and alkenyl groups having 6 to 20 carbon atoms, Z is selected from the group consisting of $SO_3H$, $PO(OH)_2$, $CH_2COOH$, $(CH_2)_2SO_3H$ and salts thereof, and n is a number of from 1 to 20, and a compound of the following general formula (II):

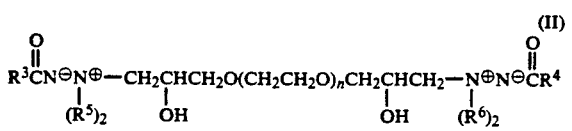

wherein $R^3$ and $R^4$ are independently selected from alkyl and alkenyl groups having 5 to 19 carbon atoms, $R^5$ and $R^6$ are independently selected from alkyl groups having 1 to 4 carbon atoms, and n is a number of from 1 to 20, wherein the relative proportion of compound (I) to compound (II) is in the range from 100:0 to 0:100, w/w, and wherein said agent is useful as a surface-active agent.

2. The surface-active agent of claim 1, wherein said alkyl or alkenyl group in formula (I) contains 6 to 12 carbon atoms.

3. The surface-active agent of claim 1, wherein said letter n in formula (I) is a number from 1 to 5.

4. The surface-active agent of claim 1, wherein said salt in formula (I) is selected from the group consisting of an alkali metal salt, an alkaline earth metal salt, an ammonium salt, and an organic alkali salt.

5. The surface-active agent of claim 4, wherein said organic alkali salt is selected from the group consisting of monoethanolamine, diethanolamine, triethanolamine, and trimethylamine.

6. The surface-active agent of claim 4, wherein said salt in formula (I) is an alkali metal salt.

7. The surface-active agent of claim 1, wherein said $R^3$ or $R^4$ alkyl or alkenyl group in formula (II) contains 5 to 11 carbon atoms.

8. The surface-active agent of claim 1, wherein said letter n in formula (II) is a number from 1 to 5.

9. The surface-active agent of claim 1, wherein said $R^5$ or $R^6$ alkyl group in formula (II) contains 1 to 3 carbon atoms.

10. The surface-active agent of claim 1, further comprising a surface-active agent selected from the group consisting of an anionic, nonionic, cationic, and ampholytic surface-active agent.

11. The surface-active agent of claim 10, wherein said nonionic surface-active agent is selected from the group consisting of a fatty acid glycerine ester, a sorbitan fatty acid ester, a sucrose fatty acid ester, a polyglycerine fatty acid ester, a higher alcohol ethylene oxide adduct, a single long chain polyoxyethylene alkyl ether, a polyoxyethylene alkyl allyl ether, a polyoxyethylene lanolin alcohol, a polyoxyethylene fatty acid ester, a polyoxyethylene glycerine fatty acid ester, a polyoxyethylene propylene glycol fatty acid ester, a polyoxyethylene sorbitol fatty acid ester, a polyoxyethylene castor oil or hardened castor oil derivative, a polyoxyetylene lanolin derivative, a polyoxethylene fatty acid amide, a polyoxyethylene alkyl amine, an alkanol amid, and an alkylamine oxide.

12. The surface-active agent of claim 10, wherein said anionic surface-active agent is selected from the group consisting of a fatty acid soup, an ether carboxylic acid and salt thereof, an alkane sulfonate salt, an α-olefin sulfonate salt, a sulfonate salt of a higher fatty acid ester, a higher alcohol sulfate ester salt, a phosphate ester salt, a condensate of higher fatty acids and amic acids, and a collagen hydrolysate derivative.

13. The surface-active agent of claim 10, wherein said cationic surface-active agent is selected from the group consisting of an alkyltrimethylammonium salt, a dialkyldimethylammonium salt, an alkyldimethylbenzylammonium salt, an alkylpyridinium salt, an alkylisoquinolinium salt, benzethonium chloride, and an acylamino acid type cationic surface-active agent.

14. The surface-active agent of claim 10, wherein said ampholytic surface-active agent is selected from the group consisting of an amino acid, betaine, a sulfate ester, sulfonic acid, phosphate ester, an imidazoline type ampholytic surface-active agent, soybean phospholipid, and yolk lecithin.

15. The surface-active agent of claim 1, further comprising an auxiliary additive.

16. The surface-active agent of claim 15, wherein said auxiliary additive is selected from the group consisting of an inorganic salt such as Glauber salt and common salt, a builder, a humectant, a solubilizing agent, a UV absorber, a softener, a chelating agent, and a viscosity modifier.

17. The surface-active agent of claim 1, wherein said compound of formula (I) is selected from the group consisting of $$C_8H_{17}OCH_2CHCH_2OCH_2CH_2OCH_2CHCH_2OC_8H_{17},$$
$$\phantom{xxxxxx}|\phantom{xxxxxxxxxxxxxxxxxxxx}|$$
$$\phantom{xxxxx}OSO_3Na\phantom{xxxxxxxxxxxx}OSO_3Na$$

-continued $$C_{10}H_{21}OCH_2CHCH_2OCH_2CH_2OCH_2CHCH_2OC_{10}H_{21},$$
$$\phantom{xxxxxx}|\phantom{xxxxxxxxxxxxxxxxxxxxx}|$$
$$\phantom{xxxxx}OSO_3Na\phantom{xxxxxxxxxxxxx}OSO_3Na$$

$$C_8H_{17}OCH_2CHCH_2OCH_2CH_2OCH_2CHCH_2OC_8H_{17},$$
$$\phantom{xxxxx}|\phantom{xxxxxxxxxxxxxxxxxxxxx}|$$
$$\phantom{xxxx}OPO(ONa)_2\phantom{xxxxxxxxxxx}OPO(ONa)_2$$

$$C_{10}H_{21}OCH_2CHCH_2OCH_2CH_2OCH_2CHCH_2OC_{10}H_{21},$$
$$\phantom{xxxxx}|\phantom{xxxxxxxxxxxxxxxxxxxxx}|$$
$$\phantom{xxxx}OPO(ONa)_2\phantom{xxxxxxxxxxx}OPO(ONa)_2$$

$$C_8H_{17}OCH_2CHCH_2OCH_2CH_2OCH_2CHCH_2OC_8H_{17},$$
$$\phantom{xxxxx}|\phantom{xxxxxxxxxxxxxxxxxxxxx}|$$
$$\phantom{xxxx}OCH_2COONa\phantom{xxxxxxxxx}OCH_2COONa$$

$$C_{10}H_{21}OCH_2CHCH_2OCH_2CH_2OCH_2CHCH_2OC_{10}H_{21},$$
$$\phantom{xxxxx}|\phantom{xxxxxxxxxxxxxxxxxxxxx}|$$
$$\phantom{xxxx}OCH_2COONa\phantom{xxxxxxxxx}OCH_2COONa$$

$$C_8H_{17}OCH_2CHCH_2OCH_2CH_2OCH_2CHCH_2OC_8H_{17},$$
$$\phantom{xxxxx}|\phantom{xxxxxxxxxxxxxxxxxxxxx}|$$
$$\phantom{xxx}OCH_2CH_2SO_3Na\phantom{xxxxxx}OCH_2CH_2SO_3Na$$

and $$C_{10}H_{21}OCH_2CHCH_2OCH_2CH_2OCH_2CHCH_2OC_{10}H_{21}.$$
$$\phantom{xxxxx}|\phantom{xxxxxxxxxxxxxxxxxxxxx}|$$
$$\phantom{xxx}OCH_2CH_2SO_3Na\phantom{xxxxxx}OCH_2CH_2SO_3Na$$

18. The surface-active agent of claim 1, wherein said compound of formula (II) is selected from the group consisting of $$C_9H_{19}\overset{\mathrm{O}}{\overset{\|}{C}}N^{\ominus}N^{\oplus}(CH_3)_2CH_2CHCH_2OCH_2CH_2OCH_2CHCH_2(CH_3)_2N^{\oplus}N^{\ominus}\overset{\mathrm{O}}{\overset{\|}{C}}C_9H_{19},$$

and $$C_7H_{15}\overset{\mathrm{O}}{\overset{\|}{C}}N^{\ominus}N^{\oplus}(CH_3)_2CH_2CHCH_2OCH_2CH_2OCH_2CHCH_2(CH_3)_2N^{\oplus}N^{\ominus}\overset{\mathrm{O}}{\overset{\|}{C}}C_7H_{15}.$$

* * * * *